(12) United States Patent
Smith et al.

(10) Patent No.: US 8,016,819 B2
(45) Date of Patent: Sep. 13, 2011

(54) PROTECTIVE COVER FOR A SURGICAL TOOL

(75) Inventors: Steven Smith, Renton, WA (US); Lewis V. Nevel, Lakewood, WA (US)

(73) Assignee: MicroSurgical Technology, Redmond, WA (US)

( * ) Notice: Subject to any disclaimer, the term of this patent is extended or adjusted under 35 U.S.C. 154(b) by 23 days.

(21) Appl. No.: 12/686,151

(22) Filed: Jan. 12, 2010

(65) Prior Publication Data

US 2010/0111759 A1     May 6, 2010

Related U.S. Application Data

(62) Division of application No. 11/542,523, filed on Oct. 2, 2006, now Pat. No. 7,981,108.

(51) Int. Cl.
*A61B 17/00*     (2006.01)

(52) U.S. Cl. ............... 606/1; 128/898; 206/210; 422/28
(58) Field of Classification Search ....................... None
See application file for complete search history.

(56) References Cited

U.S. PATENT DOCUMENTS

| | | | | |
|---|---|---|---|---|
| 5,389,084 A | * | 2/1995 | Horan et al. | 604/192 |
| 6,783,537 B1 | * | 8/2004 | Kuhr et al. | 606/182 |
| 2002/0125158 A1 | * | 9/2002 | High et al. | 206/370 |

* cited by examiner

*Primary Examiner* — Henry M Johnson, III
*Assistant Examiner* — Lynsey Crandall
(74) *Attorney, Agent, or Firm* — Ben J. Yorks; Irell & Manella LLP

(57) ABSTRACT

A cover that protects a tip of a surgical instrument. The tip can be placed within a housing of the cover. The housing has openings on each end that allow sterilization fluid to flow across the tip during an autoclave procedure. The tip can be placed on a handle of the cover. The handle can be rotated relative to the housing to allow for the easy insertion and removal of the tip from the cover.

3 Claims, 2 Drawing Sheets

PROTECTIVE COVER FOR A SURGICAL TOOL

CROSS-REFERENCE TO RELATED APPLICATIONS

This is a divisional of U.S. application Ser. No. 11/542,523 filed Oct. 2, 2006, now U.S. Pat. No. 7,981,108 which claims priority to U.S. Provisional Application No. 60/722,247 filed on Sep. 30, 2005.

BACKGROUND OF THE INVENTION

1. Field of the Invention

The present invention relates to a cover that protects the tip of a surgical instrument.

2. Background Information

Ophthalmic procedures are sometimes performed using surgical instruments such as forceps and ultrasonic hand pieces. The instruments typically include removable tips that must be sterilized after each procedure. Sterilization can be accomplished by placing the tip in an autoclave. The autoclave introduces a pressurized fluid that cleans the tip.

The tips of the surgical instruments are relatively small and can be cumbersome to handle. Additionally, the tips can be easily bent or otherwise damaged. To protect the surgical tips, and to facilitate handling and storage, the tips can be placed in a plastic cover. The protective cover has a single opening to allow insertion of the tip. When placed in an autoclave the single opening limits the flow of sterilization fluid. It would be desirable to provide an instrument tip cover that maximize the flow of sterilization fluid across the tip.

BRIEF SUMMARY OF THE INVENTION

A protective cover for a tip that can be attached to a surgical instrument. The cover has a housing that supports the tip. The housing may include an opening at a first end and an opening at a second end. The protective cover may have a handle that holds the tip and is pivotally connected to the housing.

DETAILED DESCRIPTION

Described is a cover that protects a tip of a surgical instrument. The tip can be placed within a housing of the cover. The housing has openings on each end that allow sterilization fluid to flow across the tip during an autoclave procedure. The tip can be placed on a handle of the cover. The handle can be rotated relative to the housing to allow for the easy insertion and removal of the tip from the cover.

Figure 1:
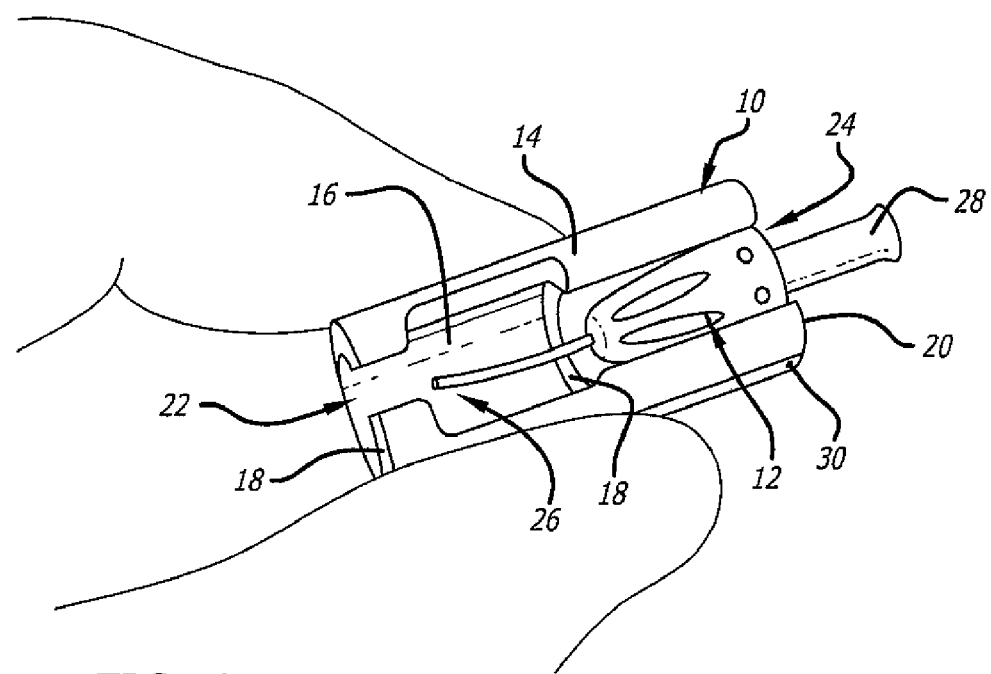
FIG. 1 is an illustration showing a tip located within a protective cover.

Referring to the drawings more particularly by reference numbers, FIG. 1 shows an embodiment of a protective cover 10. The protective cover 10 supports and protects a surgical instrument tip 12. The protective cover 10 includes a housing 14 that has a channel 16. The tip 12 is located within the channel 16 preferably at a depth so that the tip 14 cannot be damaged thru inadvertent contact.

The housing 14 includes a first end 18 and a second end 20. Each end 18 and 20 has an opening 22 and 24. The cover housing 14 also has a longitudinal opening 26 that extends across the length of the housing 14. The cover 10 and tip 12 can be placed in a sterilization chamber (not shown) such as an autoclave. The openings 22, 24 and 26 allow sterilization fluid to flow across the tip 12 with minimal fluid restriction. The cover 10 thus protects the tip 12 while allowing for effective tip sterilization.

The protective cover 10 may include a handle 28 that is pivotally connected to the housing 14. The handle 28 may have protrusions that extend into corresponding apertures of the housing to create a hinge 30. Alternatively, the hinge 30 may be created with housing protrusions that extend into corresponding apertures of the handle 28. The tip 12 is mounted to the handle 28. Both the housing 14 and handle 28 can be constructed from a molded plastic material, preferably a plastic that is optically transparent.

Figure 2:
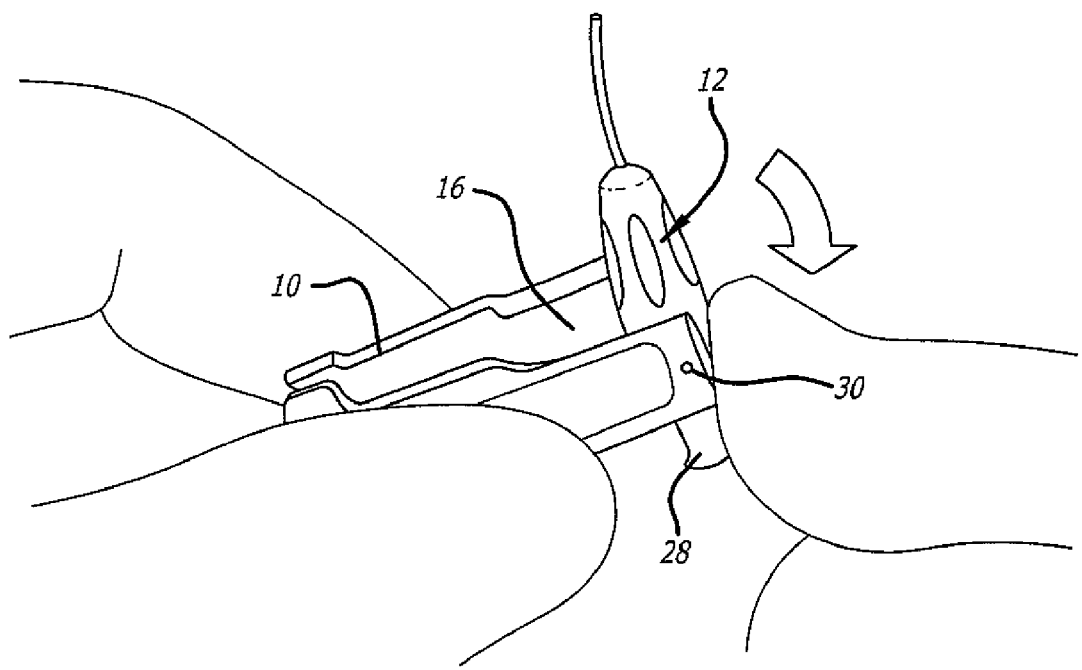
FIG. 2 is an illustration showing a handle of the cover being rotated by a user.
Figure 3:
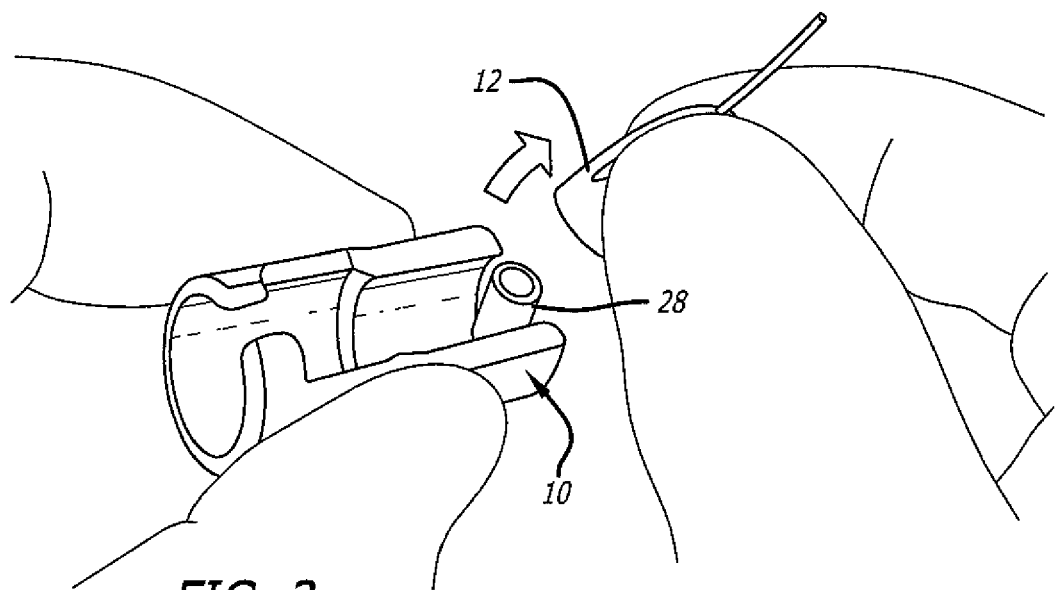
FIG. 3 is an illustration showing the tip being removed from the handle.

As shown in FIG. 2, the handle 28 can be rotated so that the tip 12 is out of the channel 16. As shown in FIG. 3 the tip 12 can be removed from the handle 28.

Figure 4:
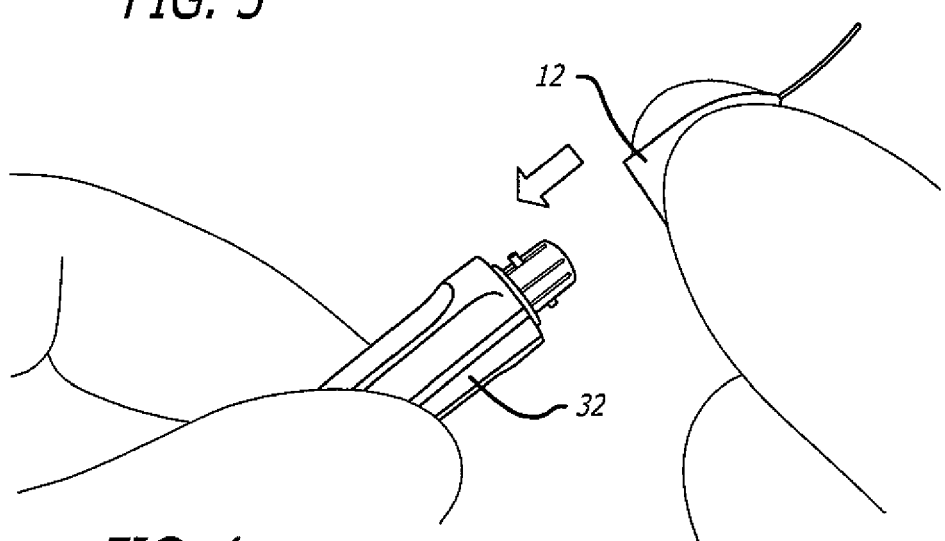
FIG. 4 is an illustration showing the tip being attached to a surgical instrument.
Figure 5:
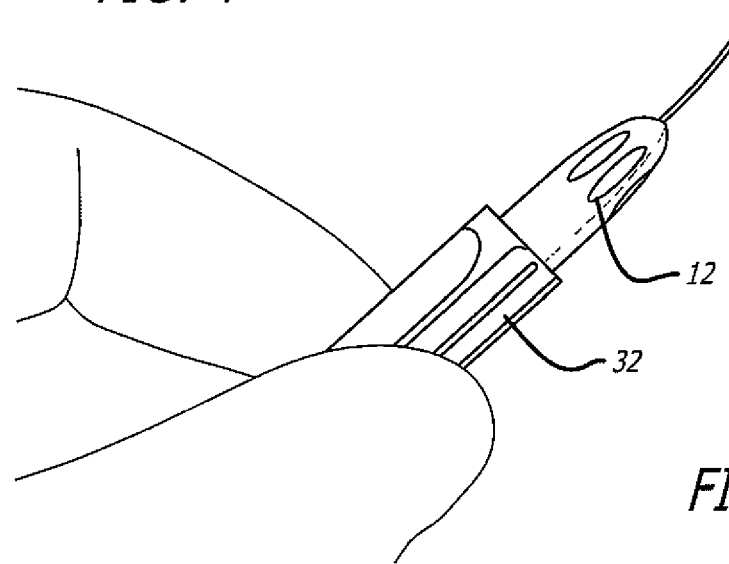
FIG. 5 is an illustration showing the tip attached to the surgical instrument.

The tip 12 can then be attached to a surgical instrument 32 as shown in FIGS. 4 and 5. After use in a surgical procedure, the tip 12 can be removed from the instrument 32. The tip 12 can then be mounted to the handle 28, rotated into the channel 16 and once again sterilized in an autoclave.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A method for sterilizing a tip that can be attached to a surgical instrument, comprising:

placing a single tip in a housing of a protective cover that is adapted to support only the single tip, the housing having an opening at a first end and a opening at a second end;

placing the tip and protective cover in a sterilization chamber;

sterilizing the tip with a sterilization fluid that flows through the openings of the protective cover; and, rotating a handle of the protective cover and removing the tip from the handle.

2. A method for removing a tip that can be attached to a surgical instrument from a protective cover, comprising:

rotating a handle of a protective cover so that a tip attached to said handle moves through a longitudinal slit of the protective cover; and, removing the tip from the handle.

3. The method of claim 1, wherein the sterilization fluid flows through a longitudinal slit of the protective cover that extends along an entire length of the protective cover.

* * * * *